United States Patent [19]

De Baere

[11] Patent Number: 4,684,468
[45] Date of Patent: Aug. 4, 1987

[54] PROCESS AND INSTALLATION FOR ANAEROBIC DIGESTION

[75] Inventor: Luc De Baere, Ghent, Belgium

[73] Assignee: Ateliers de Constructions Electriques de Charleroi, Charleroi, Belgium

[21] Appl. No.: 823,143

[22] Filed: Jan. 29, 1986

Related U.S. Application Data

[63] Continuation of Ser. No. 626,381, Jun. 29, 1984, abandoned.

[30] Foreign Application Priority Data

Jul. 1, 1983 [EP] European Pat. Off. ........ 83200980.7

[51] Int. Cl.⁴ .............................................. C02F 11/04
[52] U.S. Cl. .................................. 210/603; 210/605; 210/613; 210/195.3; 210/218; 48/197 A; 435/167
[58] Field of Search ............... 210/603, 605, 613, 631, 210/610, 630, 195.3, 197, 218; 48/197 A, 111; 435/167, 316; 71/10, 12, 13

[56] References Cited

U.S. PATENT DOCUMENTS

| | | |
|---|---|---|
| 2,190,598 | 2/1940 | Fischer ................................ 210/631 |
| 2,315,577 | 4/1943 | Bach .................................... 210/613 |
| 2,661,332 | 12/1953 | Mortenson ......................... 210/631 |
| 3,520,802 | 7/1970 | Pavia .................................... 210/631 |
| 4,255,389 | 3/1981 | Jung et al. ........................... 422/209 |
| 4,297,216 | 10/1981 | Ishida et al. ......................... 210/603 |
| 4,318,993 | 3/1982 | Ghosh et al. ........................ 210/631 |
| 4,511,370 | 4/1985 | Hunziker et al. ................... 210/603 |

FOREIGN PATENT DOCUMENTS

| | | |
|---|---|---|
| 301076 | 3/1916 | Fed. Rep. of Germany . |
| 601668 | 9/1934 | Fed. Rep. of Germany . |
| 3015239 | 10/1981 | Fed. Rep. of Germany . |
| 57-75194 | 5/1982 | Japan .................................. 210/605 |
| 1110352 | 4/1968 | United Kingdom . |

OTHER PUBLICATIONS

A Joint Committee of the Water Pollution Control Federation and the American Society of Civil Engineers, "Wastewater Treatment Plant Design", 1977, pp. 519–521, WPCF, Washington, D.C.

Primary Examiner—Benoît Castel
Attorney, Agent, or Firm—Schwartz, Jeffery, Schwaab, Mack, Blumenthal & Evans

[57] ABSTRACT

In the process of treating organic materials comprising a preparation phase in which the organic material to be digested is mixed with an appropriate inoculant and introduced into an anaerobic digester (6), the organic materials are mixed with the inoculant in a mixer (3) in order to form a solid-appearing mass which is introduced into the digester (6) and is extracted thereform after a period of less than 50 days; a part equal to at least one-third of the material extracted from the digester (6) is recycled to the inlet and mixed by kneading with a quantity of fresh organic material less than twice the recycled quantity, the quantity of fresh organic material being pretreated as needed by a drying or by humidification in a manner such that the mass leaving the mixer (3) has a rate of humidity between about 55% and 75%.

12 Claims, 1 Drawing Figure

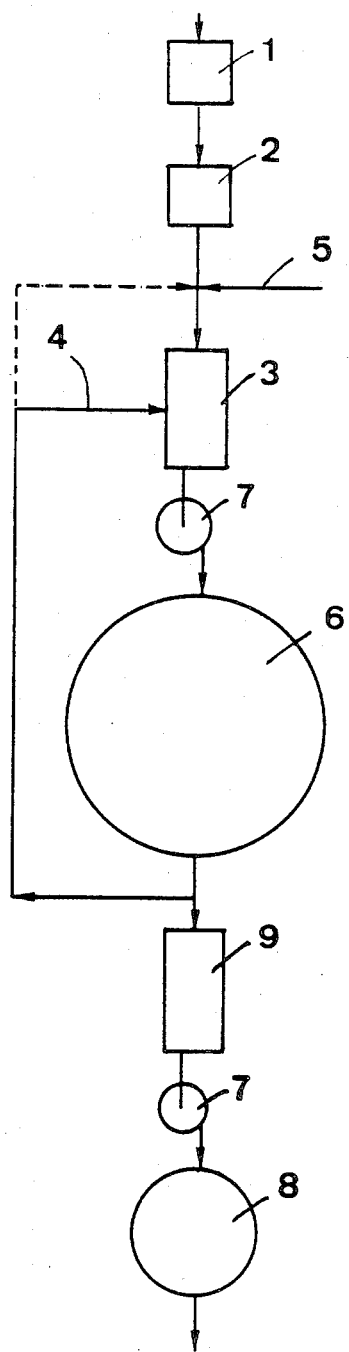

PROCESS AND INSTALLATION FOR ANAEROBIC DIGESTION

This application is a continuation of application Ser. No. 626,381, filed June 29, 1984, now abandoned.

This invention relates to a process and installation for the anaerobic digestion of organic waste material, such as household refuse and the like for the production of a useable gas, known as "biogas" which is chiefly methane.

BACKGROUND AND OBJECTS OF THE INVENTION

It is already known to produce biogas by means of organic materials and particularly garbage obtained from the collection of household refuse by means of an anaerobic digestion eventually aided by an appropriate inoculation. According to one such known process, the garbage provided from the collection is first crushed or pulverized and sorted to remove the heavy portions, such as metals, glass, and the like. The lighter parts, comprising essentially organic materials, are mixed with water, sewage sludges, liquid manure, etc., and/or still another appropriate inoculant, and subjected to anaerobic digestion processes in order to produce biogas from a liquid mass, comprising in general at least 15% dry material.

According to a process described in French Pat. No. 2,327,974, one process for treating household waste is known in which the preliminarily crushed waste is moistened by means of a liquid inoculant during fermentation, and the liquid inoculant is recycled. This known process produces methane, and necessitates a fermentation period of 15 to 30 years. After a time of about 15 years, the refuse is usable as fertilizer, but after 30 years such use is no longer possible.

The present invention has as an object a process of anaerobic composting or anaerobic digestion, at great speed, of solid or solid-like organic material, in which the degradation by anaerobic digestion is almost complete and is accomplished in a matter of several days up to 3 months. Another object of the invention comprises an anaerobic digestion process for nonliquid organic materials in which the undesirable side effect of initial acidification of the organic material is eliminated.

Moreover, the invention makes it possible to obtain a residual product in the form of stabilized, or substantially stabilized compost which is odorless or substantially odorless, not needing further treatment.

DESCRIPTION OF THE INVENTION

According to the invention, a process for the treatment of organic materials comprises a preparation phase in which the organic material to be subjected to fermentation is mixed with an appropriate inoculant and introduced into an anaerobic digester, the process is characterized in that the organic materials are mixed with the inoculant for forming a mass of solid appearance which is introduced into the digester and is removed therefrom after a period of less than 50 days, subsequently a part equal to approximately one-third and preferably equal to at least two-thirds of the mass removed from the digester is recycled to the beginning and mixed by kneading with the fresh organic material, in order to pretreat, by drying as well as by humidifying in such a manner that the mass introduced into the digester is a mass which comprises between 20 and 45% of dry material. The non-recycled part of the mass removed form the fermenter may be used as moist compost, either directly, or subsequently dried, or after passage through a complimentary digester.

The invention may be applied, for example, to organic materials obtained from the collection of household waste or refuse, to beet waste, to potato waste, the solid parts coming from a fluid after being removed from centrifugation or pressing, etc. In the case of household wastes, the waste is ground and separated from the heavy parts such as metals, glass, etc., in order to isolate the parts formed almost exclusively from solid organic material.

DESCRIPTION OF THE DRAWING

The invention is described below with reference to one example of a form of carrying out the invention represented schematically in the single FIGURE of drawings attached.

DESCRIPTION OF THE PREFERRED EMBODIMENTS

In the process shown schematically in the attached drawing, the waste material provided from the collection of household refuse is introduced into a grinder 1. At the exit from the grinder 1, the heavy particles, if there are any, notably metals, glass, etc., may eventually be separated from the organic particles in a separator 2. It is apparent that in the case where the refuse is purely organic, for example in beet wastes, such a separator is not indispensable.

A separation of certain components of the rubbish may also take place in advance of the grinding phase, for example, extraction of ferromagnetic metals in a known manner.

The mass of organic matter is introduced into a mixer 3 simultaneously with a determined quantity of sludge capable of breaking down the organic matter into methane gas and acetic-group containing compounds or inoculated sludge introduced through conduit 4 and eventually an application of water, preferably hot, provided through a conduit 5. The conduit 4 may be joined either upstream of the mixer 3, as shown in broken lines, or through a special introduction point into the mixer 3, as shown in solid lines. The inoculation sludge is added in very large quantity, such a quantity being at least equal to one-half, and preferably twice the quantity of fresh organic material. The use of such quantities of inoculation sludge has the effect of eliminating undesirable consequences of initial acidification of the fresh organic material due to the intimate inoculation and the importance of fresh material for the inoculation mass. At any rate, the permanent use of such quantities is only possible so long as the major portion of the inoculation sludge comprises recycled sludge recovered from the exit of the digestion installation or of the compost fed by the mixer 3.

This composting installation comprises a digester 6 for high specific productivity of gas. For a daily introduction of 100 tons of waste from which heavy particles have been removed, this waste comprising 40 to 65% dry material, an introduction of water, for example 50 tons, is necessary in order to render the mass thus obtained sufficiently moist for being subjected to an anaerobic digestion for rapid fermentation. The addition of water takes place by kneading in the mixer 3. The mixer 3 thus treats a mass of which the amount of humidity is between 55 and 75%. The mixer 3 receives daily 150 tons of essentially solid, moist waste, and for example 300 tons of recycled mass.

A pump 7, for example a so-called slurry pump such as is used for pumping cement, delivers the mass of 450 tons per day leaving the mixer 3 into the digester 6 of a capacity of at least 10 times the daily arrival, for example 2,000 m³. In this digester is found, in normal operation, continuously a mass of about 1,500 tons liberating an important quantity of methane gas.

The mass supplied by the pump 7 is distributed, for example, along the upper part of the digester 6 which is in the form of a vertical cylinder, and is extracted from the bottom of the digester after a passage of time of about 3.5 days, in a proportion of about 405 tons per day, 45 tons having been transformed into biogas, principally methane and recovered in this form for an ultimate use. Of these 405 tons, 300 tons are recycled to the beginning of the mixer 3 by the conduit 4 while 105 tons are delivered towards the discharge. In this manner, the average duration of digestion of fresh organic material in the digester 65 is approximately 14 days. The 105 tons of mass carried off toward the discharge may be used as it is as fertilizer in the form of compost, eventually after seasoning and drying to reduce its rate of humidity to less than 50%.

At any rate, the mass of solid appearance which is extracted from the digester 6 has a moisture content between 55% and 75% and is preferably subjected to a final digestion in a complementary digester 8 of a capacity of at least 5 times the amount of material arriving daily, for example 1,000 m³ from which approximately 100 tons of the mass is extracted after a passage of time of about 7 days, 5 tons having been transformed into biogas. One thus achieves a transformation of 100 tons dry household waste within 21 days. The production of pure methane by means of the described process is very high and is on the order of 250 m³ of methane per ton of dry degradable material. The capacity of the digesters 6 and 8 may always remain less than respectively 50 and 25 times the daily arrival rate.

During the transfer from the digester 6 to the digester 8, the mass may traverse a mixer 9 in which a suitably proportioned aeration stimulates a certain production of acids favorable to the ultimate anaerobic digestion in the digester 8.

The product leaving the digester 8 is completely inactive and without odor; it forms an excellent compost.

A portion of gas recovered in the digesters 6 and 8, after passage through a compressor (not shown) may be reinjected into the bottom of each digester in order to avoid too dense a packing of the solid-appearing mass and to favor release of the product gas. The recycled gas may serve to regulate the temperature in the digester by a heating or a cooling before injection into the bottom of the digester.

It is also possible to inject a small quantity of air at a suitable proportion at the same time that one injects the recycled gas in order to bring about a small aeration of the mass at the bottom of the digester. It has been observed here that it is not a question of proceeding with aerobic digestion, but still a process of anaerobic digestion in which the quantity of air admitted must be maintained very slight. In this case, this presence of air stimulates degradation of the mass in the digesters and brings about a reduction in their temperature.

The inoculation sludge may be made up partially or preferably entirely of recycled material. However, upon the condition that one may dispose permanently of a large quantity of inoculation sludge provided from a different installation, for example an anaerobic treatment installation for sewage waste, the inoculation sludge may be comprised either partially or completely by that furnished by this different installation. At any rate, an introduction of methanogenic inoculation sludge provided from a foreign source is useful and is even indicated at the start of the installation described hereinabove, up to the point where the pH in the digesters 6 and 8 has arrived at a value between about 7 and 8.

Instead of water serving for the humidification and introduced by the conduit 5, it is also possible to use an inoculating liquid provided from a methanogenic source.

The process described is useful as well in the case of methanogenic reactions at about 35° C. up to about 60° C. The transportation of the humid mass to or from the digesters 6 or 8 may be carried out by means of slurry pumps or concrete pumps.

The recovered water from the drying of the compost leaving the digester 6 or the digester 8 may also be partially or totally recycled by means of the conduit 5. A limit may be imposed on this recycling if the water carries salt which would interfere with or inhibit the fermentation.

The gas produced in the installation may be used in an electrical generation system from which the escaping may be applied for drying of the compost leaving the digesters 6 or 8.

I claim:

1. A process for anaerobic digestion of solid-like organic material, comprising the steps of:
   mixing and kneading the solid-like organic material with an inoculant and forming thereby solid-like mass having a water content of from about 55% to about 75% by weight;
   feeding the solid-like mass having a water content of from about 55% to about 75% by weight to an anaerobic digester;
   anaerobically digesting said solid-like mass having a water content of from about 55% to about 75% by weight in said digester for a period of less than about 50 days;
   recovering biogas produced during said digestion step, said biogas being the byproduct of anaerobic digestion;
   extracting the digested mass having a water content of from about 55% to about 75% by weight from said digester;
   recycling at least one third by weight of said extracted, digested mass to said mixing step, said recycled mass acting as said inoculant; and
   removing the non-recycled digested mass from the process.

2. A process as claimed in claim 1, said process further comprising drying or humidifying said solid-like organic material prior to said mixing step, said organic material having a water content thereby of from about 55% by weight to about 75% by weight.

3. A process as claimed in claim 2, wherein about two thirds by weight of said extracted, digested mass is recycled to said mixing step, and wherein said anaerobic digestion step is carried out in less than about 25 days.

4. A process as claimed in claim 3, wherein said process includes the step of further digesting said non-recycled digested mass.

5. A process as claimed in claim 4, wherein the pH of said non-recycled digested mass during said further digestion is from about 7 to about 8.

6. A process as claimed in claim 3, said process including the step of aerating said solid-like mass during said anaerobic digestion step.

7. A process as claimed in claim 1, wherein about two thirds by weight of said extracted, digested mass is recycled to said mixing step, and wherein said anaerobic digestion step is carried out in less than about 25 days.

8. A process as claimed in claim 4, wherein said process includes the step of further digesting said non-recycled digested mass.

9. A process as claimed in claim 4, said process including the step of aerating said solid-like mass during said anaerobic digestion step.

10. A process as claimed in claim 1, wherein said digestion step is carried out at a temperature of from about 35° C. to about 60° C.

11. A process as claimed in claim 1, wherein the pH of said solid-like mass during the digestion step is from about 7 to about 8.

12. An apparatus for anaerobic digestion of solid-like organic material, comprising:

means for mixing and kneading a mixed organic material having a water content of from about 55% to about 75% by weight comprising fresh, solid-like organic material and recycled inoculant;

a first means for anaerobically digesting the mixed organic material having a water content of from about 55% to about 75% by weight, said first digesting means having a capacity of from about 10 to about 50 times the average daily volume of the fresh, solid-like organic material mixed in said means for mixing;

means for removing biogas from said first digesting means, said biogas being a byproduct of anaerobic digestion;

means for extracting digested material having a water content of from about 55% to about 75% by weight from said first digesting means;

means for recycling a portion of said digested material to said means for mixing, said recycled portion acting as an inoculant;

a second means for further digesting non-recycled material, said second digesting means having a capacity of from about 5 to about 25 times the average daily volume of said fresh, solid-like organic material mixed in said means for mixing;

an aeration mixer for aerating said non-recycled material prior to further digestion in said second digesting means; and means for removing non-recysled, extracted digested material from said apparatus.

* * * * *